United States Patent [19]

Gawarecki

[11] Patent Number: 5,704,370
[45] Date of Patent: Jan. 6, 1998

[54] OPERATION TABLE COVER AND METHOD OF PRODUCING THE SAME

[75] Inventor: Herbert Gawarecki, Haltern, Germany

[73] Assignee: GFM Maschinenbau GmbH, Haltern, Germany

[21] Appl. No.: 604,223

[22] Filed: Feb. 22, 1996

[30] Foreign Application Priority Data

Feb. 22, 1995 [DE] Germany ............... 195 06 046.6

[51] Int. Cl.⁶ .................................................. A61B 19/00
[52] U.S. Cl. ...................................... 128/849; 128/856
[58] Field of Search ................................ 128/849–856

[56] References Cited

U.S. PATENT DOCUMENTS

| | | | |
|---|---|---|---|
| 3,707,964 | 1/1973 | Patience | 128/856 |
| 3,747,655 | 7/1973 | Hadtke | 128/855 |
| 5,148,940 | 9/1992 | Mendise | 128/849 |
| 5,411,036 | 5/1995 | Wilkes | 128/849 |
| 5,433,221 | 7/1995 | Adair | 128/849 |

FOREIGN PATENT DOCUMENTS

| | | |
|---|---|---|
| 0290738 | 6/1992 | European Pat. Off. . |
| 3519705 | 6/1985 | Germany . |
| 3715691 | 5/1987 | Germany . |
| 4033243 | 10/1990 | Germany . |

*Primary Examiner*—Michael A. Brown
*Attorney, Agent, or Firm*—Michael J. Striker

[57] ABSTRACT

An operation table cover is composed of a foil hose of thermoplastic material with a closed bottom region and an open head region provided with a circumferential reversed rim, with side edges closed by welding seams. The operation table cover is formed so that despite its substantially refuse-free manufacture, it can be fitted over the supporting surface of an operation table with a simple handling. For this purposes the side edges in the vicinity of the bottom region and directly under the reversed rim are provided with inwardly directed offset regions, and the reversed rim has the same width as the central region of the foil hose located between the offset regions.

17 Claims, 8 Drawing Sheets

OPERATION TABLE COVER AND METHOD OF PRODUCING THE SAME

BACKGROUND OF THE INVENTION

The present invention relates generally to an operation table cover and a method of producing the same.

More particularly, it relates to an operation table cover which is composed of a foil hose of thermoplastic material with a closed bottom region and an open head region provided with a circumferential reversed rim and side edges connected with one another by welding seams.

Operation table covers of the above mentioned general type are known in the art. Some of such operation table covers are disclosed in the patent document EP 0 290 738 and DE 37 15 691. In these operation table covers the width of the reversed rim at the head end is greater than the remaining region of the hose and is offset outwardly relative to the welding seams of the side edges. Due to this design, the operation table cover during its manufacture has the disadvantage of relatively long refuse strips which extend from the lower edge of the reversed rim to the bottom region. Therefore each manufacturer puts its efforts to produce such an operation table cover which overlaps the supporting surface serving as the operation table narrowly and also accurately and at the same time produces minimum refuse cuts. These two requirements substantially contradict one another. It is to be understood that the operation table cover with the above mentioned features has further handling disadvantages in that its reversed rim can be relatively easily fitted over a support surface which serves as the operation table, however the subsequent long sections under its reversed rim up to the bottom region must be pulled over the supporting surface with overcoming of relatively great friction forces. This friction is increased by the unpleasant property of the synthetic plastic foil that during its reversing step it frequently sticks in the partial regions of its inner sides to the supporting surface.

A further operation table cover of this type is disclosed in the patent document DE 35 19 705. Here, the greater width of the reversed rim is maintained so that the inner width of the foil hose in the region of the reversed rim is expanded relative to the remaining region of the foil hose. This expansion of the reversed rim requires a machine device inside the foil hose, which is difficult to handle and the above mentioned continuous expansion can be obtained with substantial difficulties since the elasticity limit of the foil material must be first overcome in the partial regions. Furthermore, the manufacturing temperature is dependent on the material of the foil.

Finally, the patent document DE 40 33 243 discloses an operation table cover in which the reversed rim has the same width as the foil hose, and with its free end to the reversed rim composed of at least two layers it is folded with the outwardly located layer in direction toward the opening in the head region. This operation table cover can be stretched faster and with lower force over the operation table than the above described covers. However, in practice it is not used since the medical personnel as a rule is not ready to change a conventional handle of a known operation table cover to another product.

SUMMARY OF THE INVENTION

Accordingly, it is an object of the present invention to provide a operation table cover and a method of producing the same, which avoids the disadvantages of the prior art.

More particularly it is an object of the present invention to provide an operation table cover of the above mentioned type which can be manufactured substantially without refuse and at the same time is easy to handle during stretching over the supporting surface of an operation table.

In keeping with these objects and with others which will become apparent hereinafter, one feature of the present invention resides, briefly stated, in an operation table cover in which the side edges in the vicinity of the bottom region and directly under the reversed rim are provided with inwardly directed offset regions, and the reversed rim has the same width as the central region of the foil hose located between both offset regions.

When the operation table cover is designed in accordance with the present invention, the foil hose has no longer narrow places in its central region but instead has the narrow places in its offset regions, and the whole relatively long central region as well as the reversed rim can be conveniently pulled over the supporting surface of an operation table. Furthermore, this operation table cover is characterized by a substantially refuse-low manufacture since the refuse strips have a limited size corresponding to the size of the relatively small offset regions.

In accordance with a further feature of the present invention the length of the offset regions in the side edges under the reversed rim is insignificantly greater than the length of the reversed rim. The length of the offset regions of the side edges in the vicinity of the bottom region is either equal or insignificantly smaller or greater than the length of the reversed rim. In view of these relative dimensions of the length of the offset regions and the reversed rim, the bottom region can be displaced over the reversed rim relatively light before it is reduced by further transverse longitudinal folding to use-ready folding packs. For these reasons the width of the offset regions under the reversed rim is formed so that it is equal to the width of the offset region in the vicinity of the bottom region.

For reducing a breaking risk as a result of notch actions, the ends of the offset regions merge to the adjoining, projecting side edges of the central region and the reversed rim in form of a quarter circle. Depending on the type of manufacture, the bottom region of the operation table cover can be closed either by a folding edge or by a welding seam.

The operation table covers in accordance with the patent documents EP 0 290 738 and DE 37 15 691 are composed of a foil hose of thermoplastic material. They are closed at the longitudinal edge forming the bottom region of the operation table cover and open at the longitudinal edge forming the head region, and in the transporting longitudinal direction pulled by pulling rollers or bands, provided at regular distances on an outer side with fibrous blanks and then provided with transversely extending welding seams and recesses. Then the foil hose is provided with a reversed rim after longitudinal folding in the central region as well as two longitudinal folds at the opposite sides on its head region, and its side edges are each connected by a welding seam. In this known process after applying the fibrous blank, which is no longer necessary in an increasing number of operation table covers, the welding seams extending transversely to the transporting direction are formed in the foil hose and extend to the lower edge of the reversed rim. Between this lower edge of the reversed rim and the bottom region the neighboring blanks for the operation table cover have no connection. After a longitudinal folding in the central region as well the longitudinal folds at the two opposite sides in its head region, the foil hose between the individual blanks for the operation table cover has a connection only in its head region. Before the side edges of the reversed rim are connected with one another by a welding seam and simultaneously the blanks are separated from one another, due to friction as well as mass inertia during long transportation a slack of a subsequent blank can occur, and thereby a welding of a head region of one operation table cover with a bottom region of a preceding operation table cover can lead to rejected products.

In order to avoid such rejected products as well as for producing the inventive operation table cover, the method in accordance with the present invention includes the following features:

a) The foil hose for forming the offset regions at the side edges of the operation table cover under the reversed rim and in the vicinity of the bottom region is provided with a separating welding, b) in the central region of the side edges between both offset regions, the foil hose is provided with a perforation welding seam extending transversely to a longitudinal transporting direction and is closed at both sides by welding, and c) the reversed rim, before separation of the individual operation table covers, is provided on its both side edges with perforation welding seams and closed at both sides by welding seams.

Because of the feature a) the relatively small offset regions are produced by a separating welding, while because of the features b) and c) the individual blanks of the operation table cover remain connected with one another until their separation both in the relatively long central region as well as at the reversed rim by perforation welding seams. Thereby until their separation, a uniform and slack free transportation of the individual operation table covers assembled with one another is guaranteed.

The perforation welding seams are preferably identically separated in the central region and at the reversed rim of the operation table cover.

In accordance with a first embodiment, the operation table covers after their separation are reduced by further longitudinal and transverse folding to ready to use folding packs so that they can be submitted to the consumer in the same form as has been done for many years for the operation table cover disclosed in the patent documents EP 0 290 738 and DE 37 15 691.

In accordance with a further, especially advantageous feature of the present invention, the assembled operation table covers after production of the perforation welding seams in the central region and at the reversed rim can be wound on a roller, from which subsequently they are tearable at their perforation welding seams in the central region and at the reversed rim. The winding on the roller eliminates the time consuming unpacking and folding during the known set packing.

The inventive method is variable both with respect to the time nd place of the individual folds as well as with respect to the timely process arrangement of the perforation welding seams in the vicinity of the reversed rim. Thus, for example in accordance with a further embodiment of the feature c) it is possible to provide the reversed rim with a perforation welding seam after a further longitudinal folding with insertion of a supporting metal plate between the central region and the reversed rim longitudinally folded on it on the side edges, and to close it at both sides by the welding seams. During this method step, the metal plate protects the central region from a further welding during the production of the welding seam of the reversed rim.

Also, the foil hose which is an initial material for the operation table cover can be produced in different ways. For example the foil hose in accordance with a first alternative can be produced from a single-layer synthetic plastic foil which is folded exactly in its center parallel to the transporting direction. In this case the folding direction forms the later bottom region of the individual operation table cover.

In accordance with the second alternative, the foil hose can be formed of two congruent individual foils arranged over one another and provided in the bottom region by a continuous welding seam parallel to the transporting direction. During the use of this method, the operation table cover has a welding seam simultaneously in its bottom region.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

As shown in FIGS. 1–10, an operation table cover 1 in accordance with the present invention, is composed of a foil hose 2 of thermoplastic material with a closed bottom region 3 and open head region 4 provided with a circumferential reversed rim 5. The operation table cover 1 is covered on its upper side 6 with an absorbing fibrous material 7 and closed at its side edges 8 and 9 by welding seams. In a constantly increasing number of operation table covers 1, the fibrous material 7 is no longer needed in view of new operation techniques with special suction devices.

Figure 2:
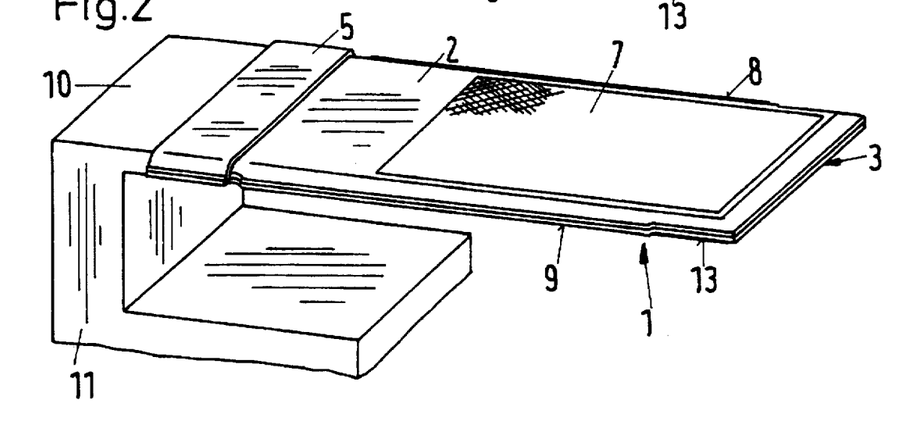
FIG. 2 is a perspective view of FIG. 1 after a partial drawing of the operation table cover over the supporting surface of an operation table.

FIG. 2 shows an operation table cover 1 which is drawn on a supporting surface 10 of an operation table 11.

Figure 3:
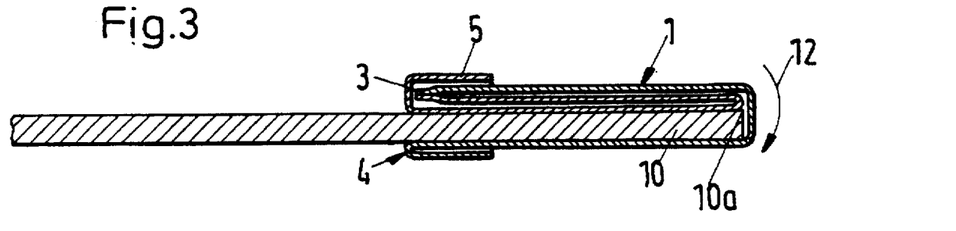
FIG. 3 is a side transverse view of the operation table cover of FIG. 2 before its drawing over the supporting surface.
Figure 4:
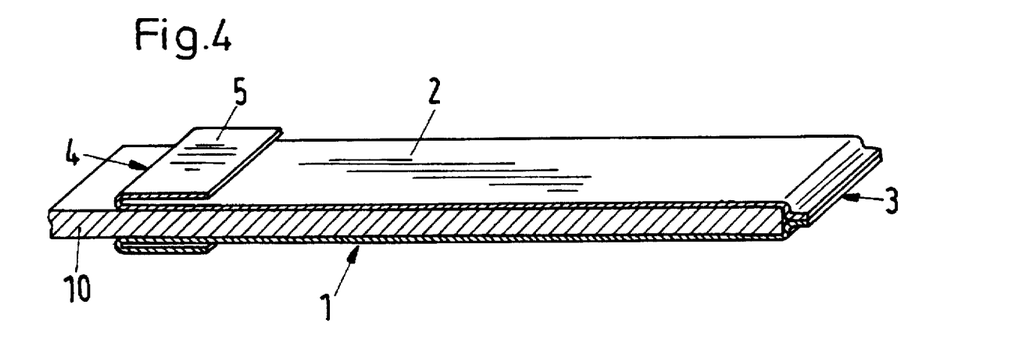
FIG. 4 is a perspective transverse view of FIG. 3 after a partial drawing of the operation table cover over the supporting surface.

In order to protect the upper surface of the fibrous material 7 from possible infectious germs shortly before the use of the operation table cover, the operational table cover 1 in FIG. 3 is displaced in the longitudinally folded condition over the supporting surface 10. The medical nurse engages with her both hands under the reversed rim 5 with holding open the head region 4 and displaces the operation table cover substantially up to its center over the supporting surface 10. In this position the fibrous material 7 is protected from infectious germs because of its folded position. During a further displacement of the operation table cover over the supporting surface 10, the further half of the folded remaining operation table cover 1 rolls in direction of the arrow XII over the edge 10a ab, until as shown in FIG. 4, the operation table cover 1 extends up to its reversed rim 5 over the supporting surface 10.

Figure 5:
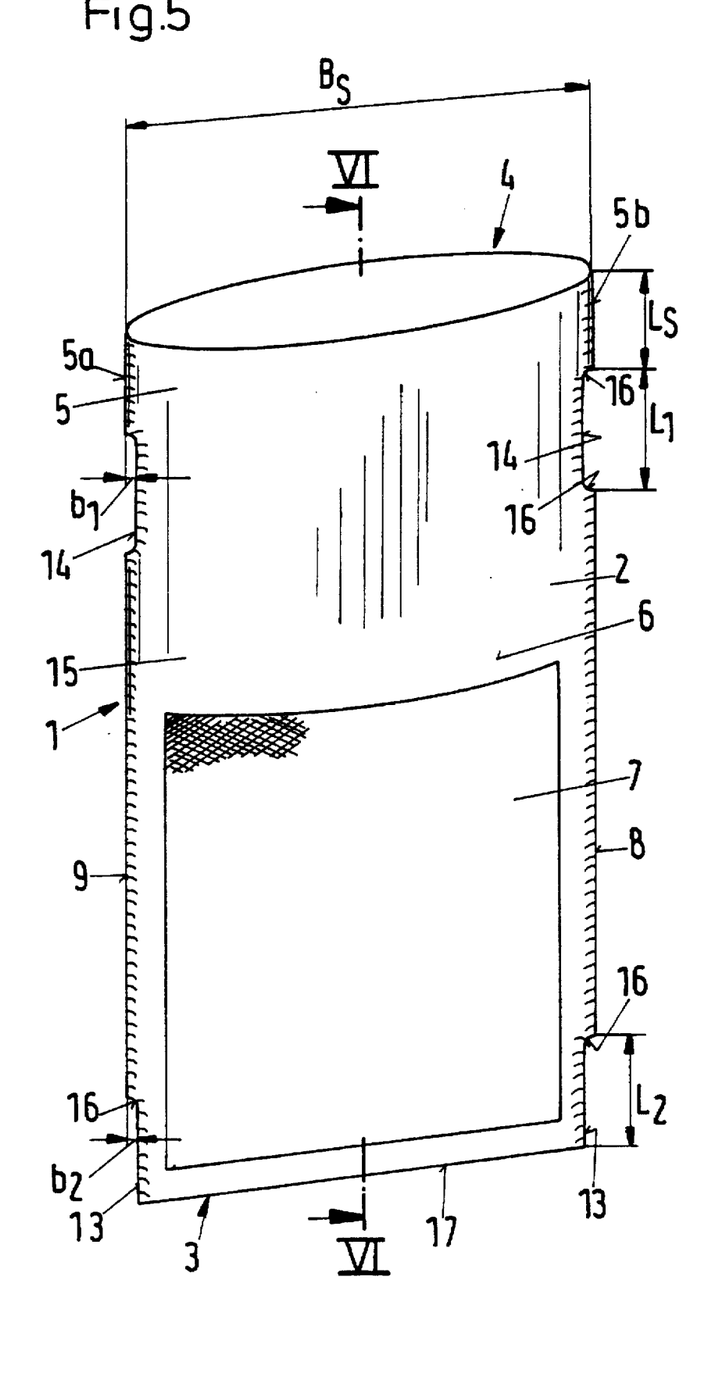
FIG. 5 is a perspective plan view of an operation table cover with an offset region under the reversed rim and a further bottom region closed by a folding edge.
Figure 6:
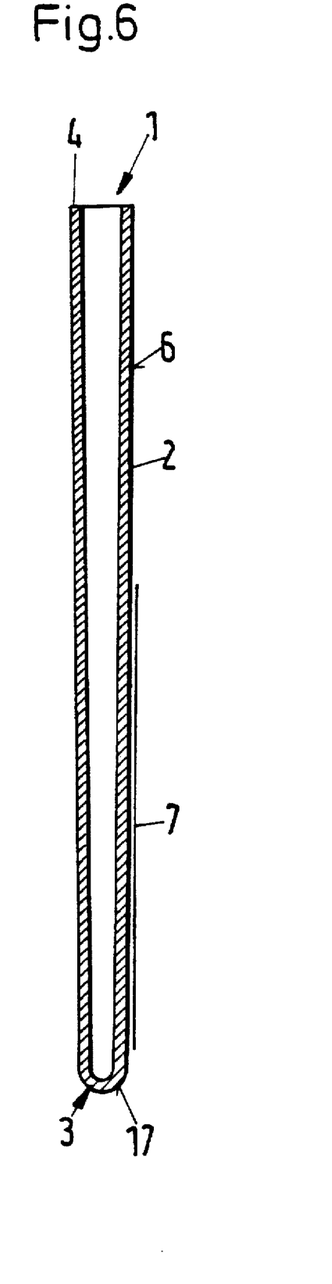
FIG. 6 is a view showing a section of the operation table cover taken along the line VI—VI in FIG. 5.

In the embodiment of FIGS. 5 and 6 the side edges 8 and 9 of the operation table cover 1 are provided in the vicinity of the bottom region 3 and directly under the reversed rim 5 with inwardly directed offset regions 13 and 14, and the reversed rim 5 has the same width $B_S$ as the central region 15 of the foil hose 2 located between both offset regions 13 and 14. The length $L_1$ of the offset region 14 of the side edges 8 and 9 under the reversed rim 5 is insignificantly greater than the length $L_S$ of the reversed rim 5. The length $L_2$ of the side edges 8, 9 in the vicinity of the bottom region 3 is either equal or significantly smaller or greater than the length $L_S$ of the reversed rim 5. Furthermore, the width $b_1$ of the offset region 14 under the reversed rim 5 is equal to the width $b_2$ of the offset region 13 in the vicinity of the bottom region 3.

Figures 7, 8:
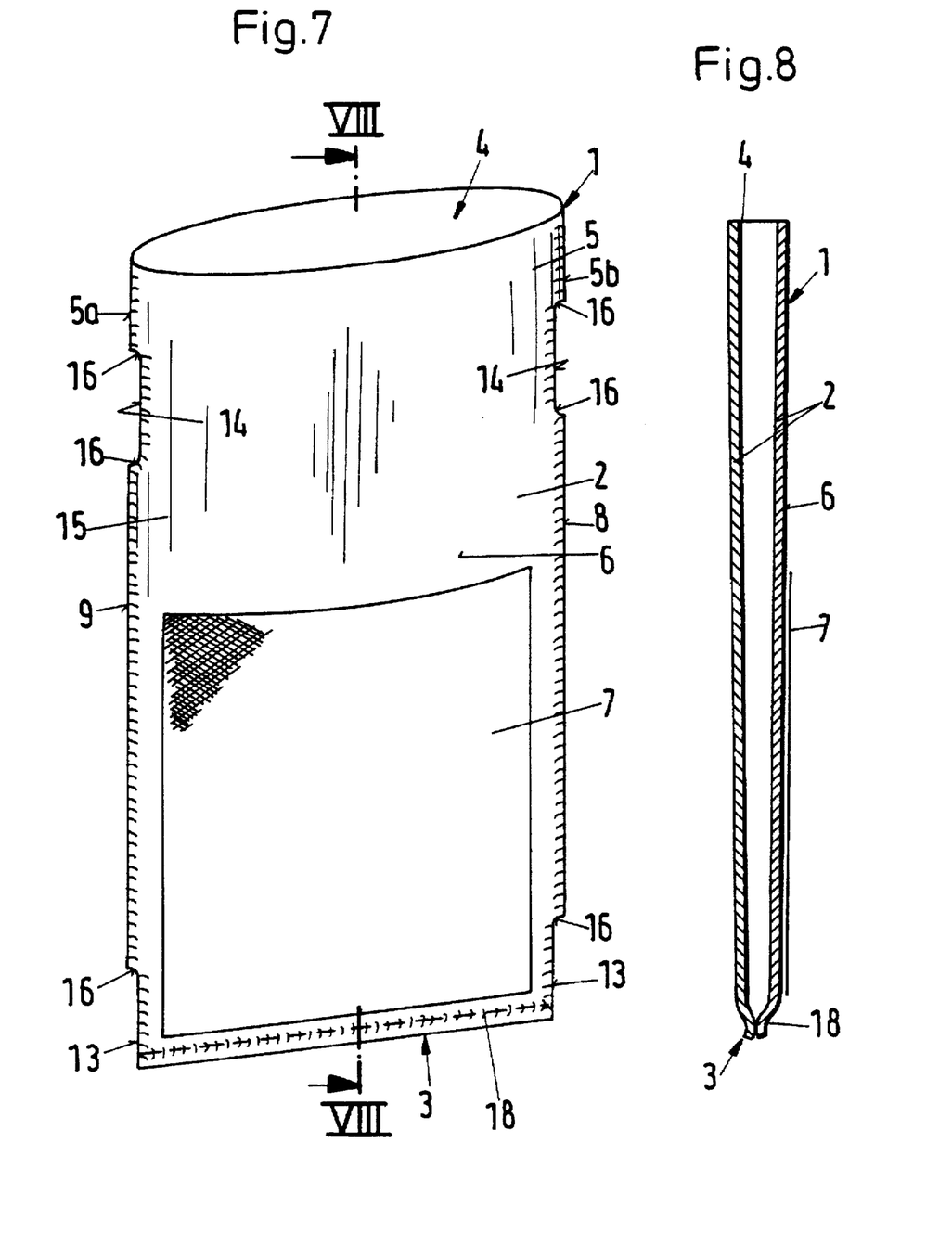
FIG. 7 is a view substantially corresponding to the view of FIG. 5, but showing a bottom region closed by a welding seam.
FIG. 8 is a view showing a section of the operation table cover taken along the lines VIII—VIII in FIG. 7.
Figure 9:
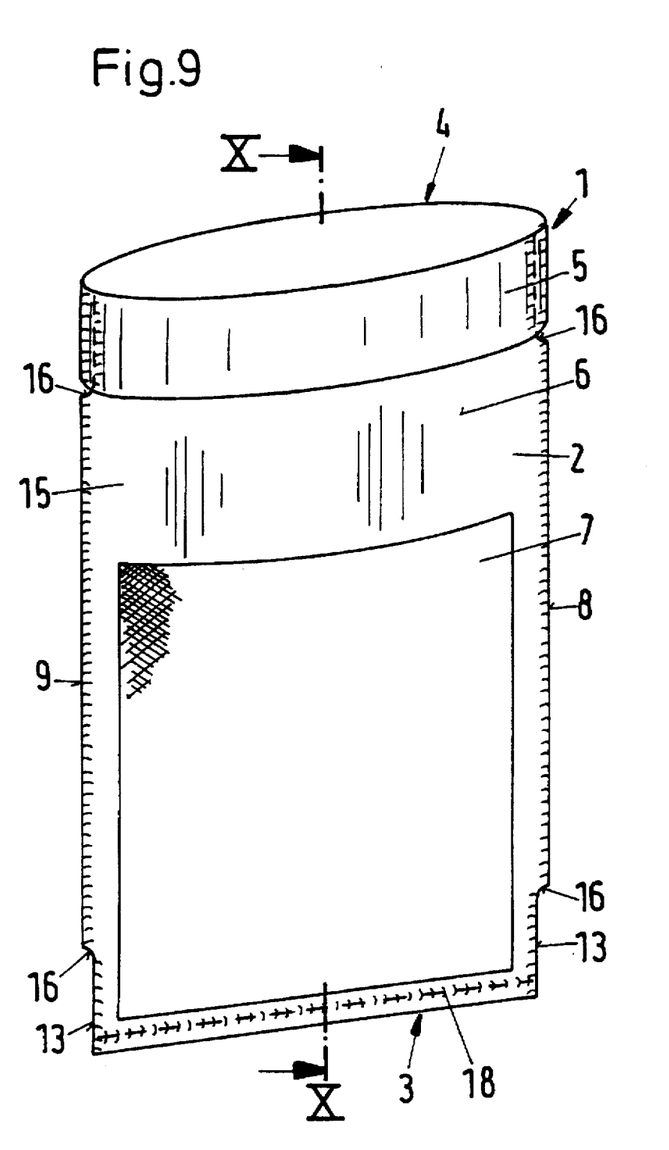
FIG. 9 is a perspective plan view of the operation table cover of FIG. 7 after producing the reversed rim by reversing of the head region.

As can be seen further from FIGS. 5, 7 and 9, the ends of the offset regions 13, 14 merge into the adjoining, projecting side edges 8, 9 of the central region 15 and the reversed rim 5 in form of a rounding 16, for example a quarter circle. Thereby the breaking risk due to notch stresses both during the manufacture as well as during stretching of the operation table cover is avoided.

The difference between the embodiment of FIGS. 5 and 6 and the embodiment of FIGS. 7–10 is that in the first embodiment the bottom region 3 is closed by a folding edge 17, while in the second embodiment it is closed by a welding seam 18.

In all embodiments of FIGS. 1–10 the side edges 8, 9 in the offset regions 13, 14 are closed by separating weldings and at the reversed rim 5 as well as in the central region 15 by a welding seam with a perforation welding seam located between them started at another location.

Figure 10:
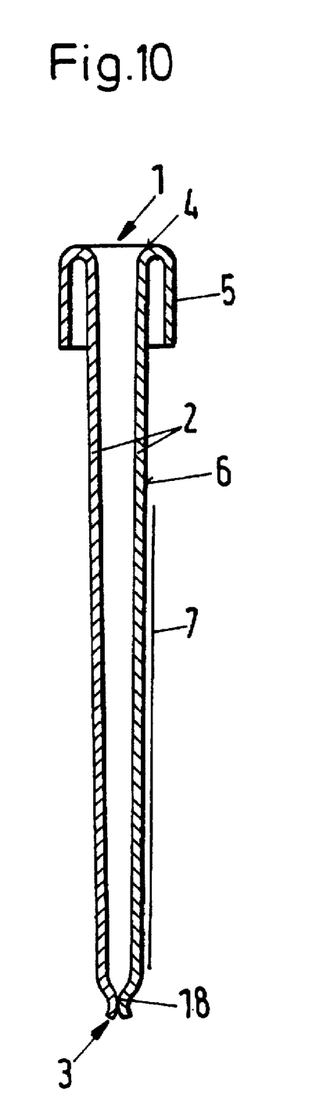
FIG. 10 is a view showing a section of the operation table cover taken along the lines X—X in FIG. 9.

In accordance with FIGS. 9 and 10, the reversed rim 5 of FIGS. 7 and 8 is turned outwardly so that with its length $L_S$ it overlaps substantially the length $L_1$ of the offset region 14. Thereby, during folding the bottom region 3 can be displaced without friction between the inner side of the reversed rim 5 and the upper surface of the foil hose 1, for protecting the fibrous material 7 from infectious germs.

In all FIGS. 1–10 as well as in the subsequent FIGS. 11–20, the corresponding parts are identified with same reference numerals.

Figure 1:
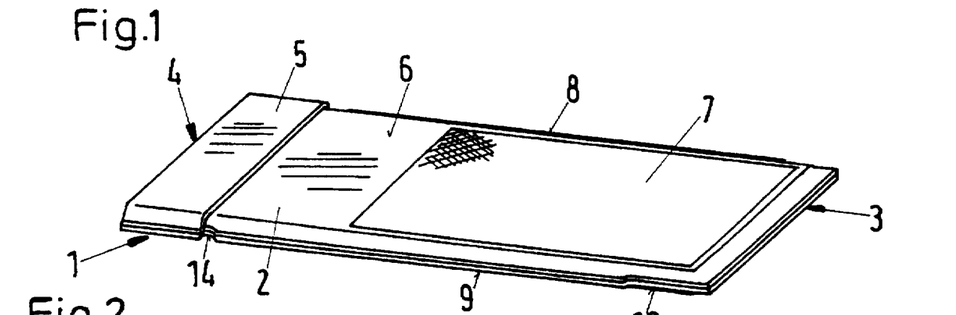
FIG. 1 is a perspective view of an operation table cover in a partially expanded position in accordance with the present invention.

As can be seen from FIGS. 5–10 in connection with FIGS. 1–2, the offset regions 13 and 14 are formed so that they can be drawn over the supporting surface 10 of an operation table 11. While at the height of these offset regions 13, 14 it is necessary to consider an increased friction during drawing of the supporting surface 10, this process is considerably facilitated in the central region 15 which is widened with its side regions 8, 9. In accordance with the prior art, the exactly opposite is the case, whereby also the handling of the inventive operation table cover 1 is improved.

Figures 11, 13, 14:
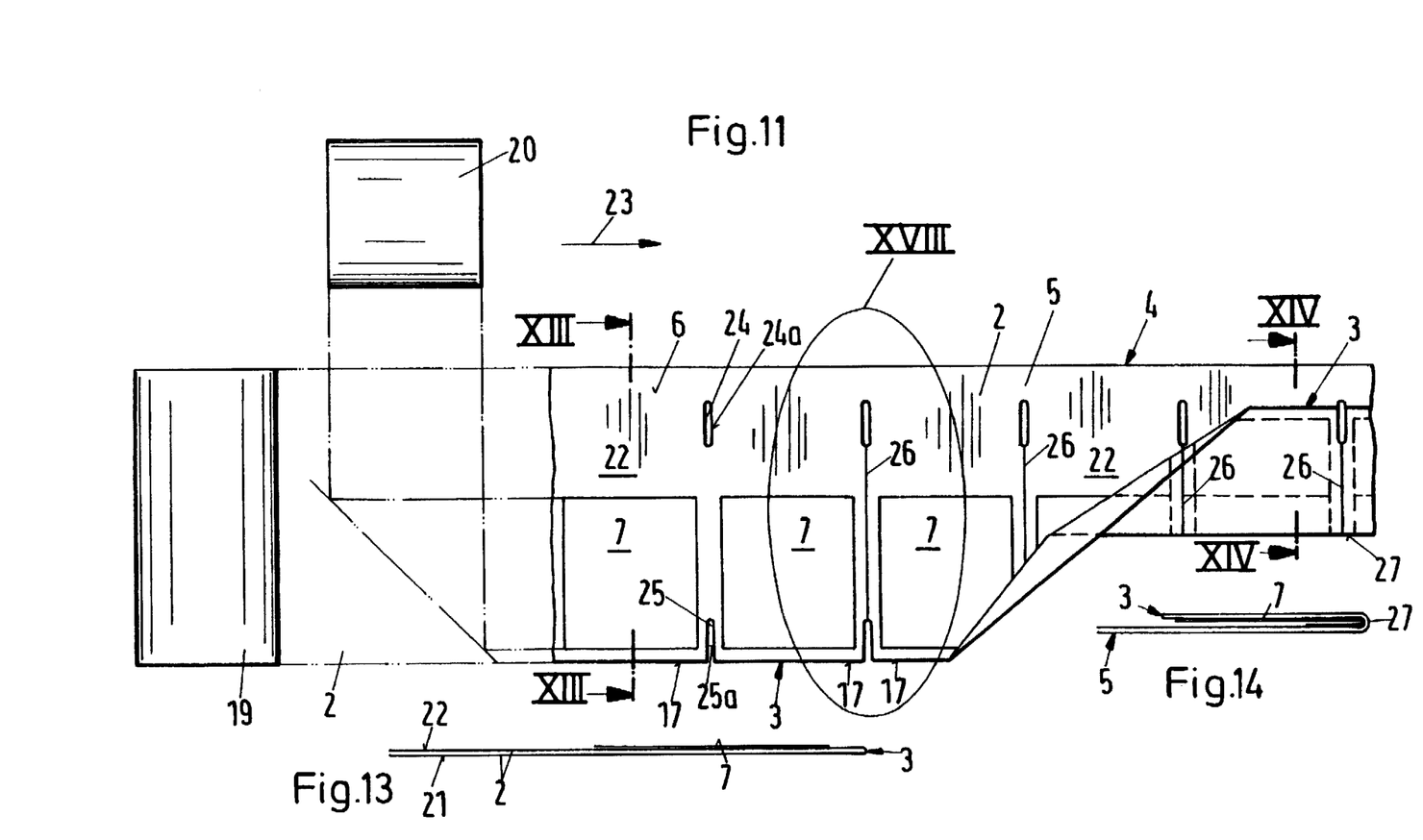
FIG. 11 is a plan view of a foil hose for producing the operation table cover in accordance with the present invention after providing offset regions by separation welding and a first longitudinal folding.
FIG. 13 is a view showing a section taken through the hose foil along the lines XIII—XIII in FIG. 11.
FIG. 14 is a view showing a section taken along the lines XIV—XIV in FIG. 11.
Figures 12, 15, 17:
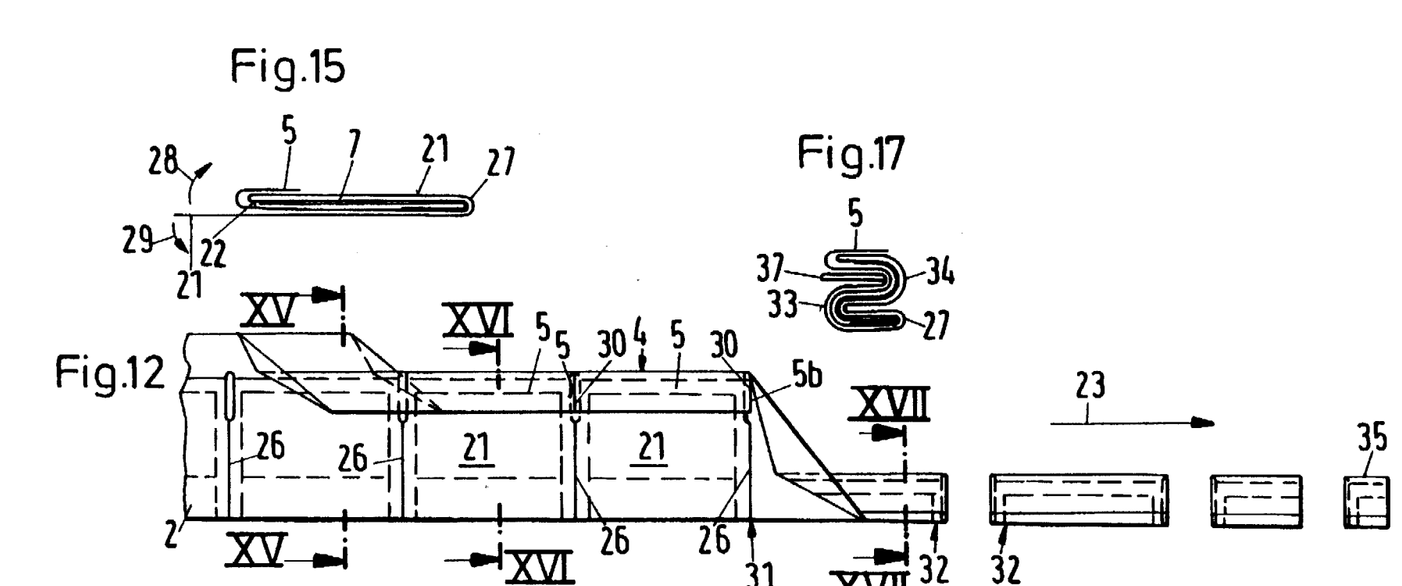
FIG. 12 is a plan view of FIG. 1 with further method steps for forming an operation table cover in form of a ready to use fold pack.
FIG. 15 is a view showing a section taken along the lines XV—XV in FIG. 12.
FIG. 17 is view showing a section taken along the lines XVII—XVII in FIG. 12.

FIGS. 11 and 12 illustrate the inventive method for producing an operation table cover, and the parts which correspond to the parts shown in FIGS. 1–10 are identified in FIGS. 11–20 with the same reference numerals.

The foil hose 2 is drawn from a supply roller 19. The foil hose in this case is produced from a single layered synthetic plastic foil which is longitudinally folded exactly in its center parallel to the transporting direction in accordance with the arrow 23 in the vicinity of the bottom region 3 of the latter operation table cover 1. Thereby the bottom region 3 is closed at this side, while to the contrary, the head region 4 is open.

Figure 18:
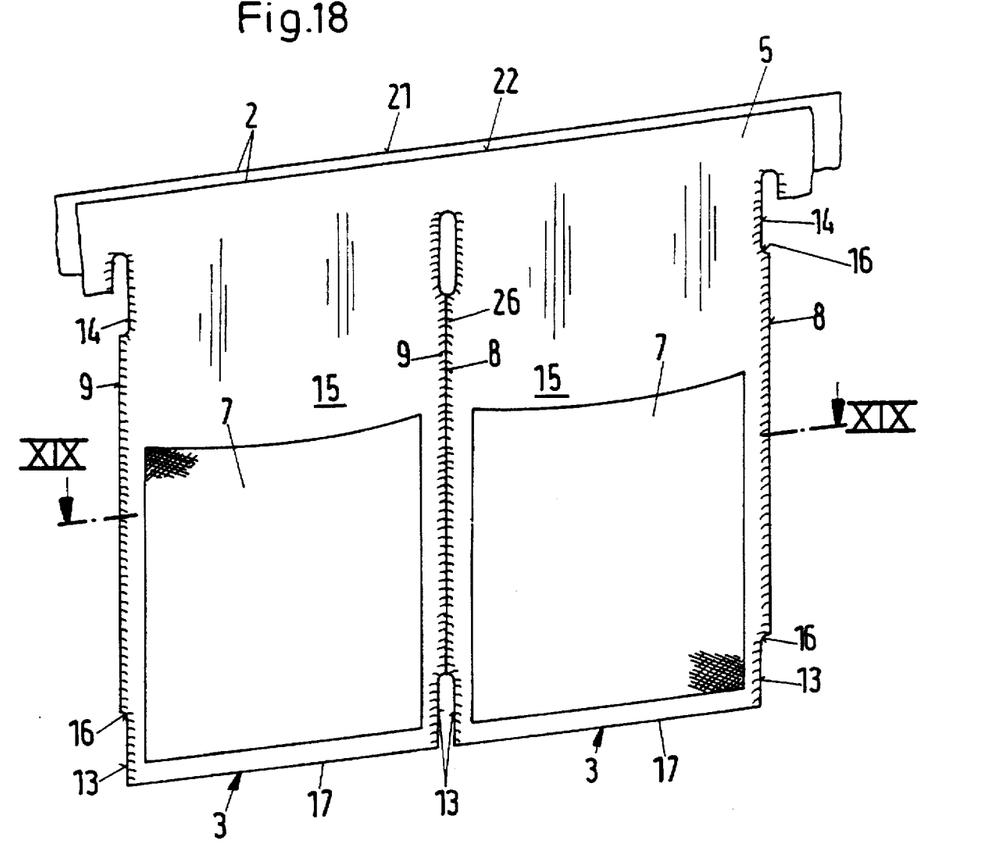
FIG. 18 is a view showing an enlarged fragment XVIII of FIG. 11 and two operation table cover assembled at their perforation welding seams in the central region and at the reversed rim.
Figure 19:
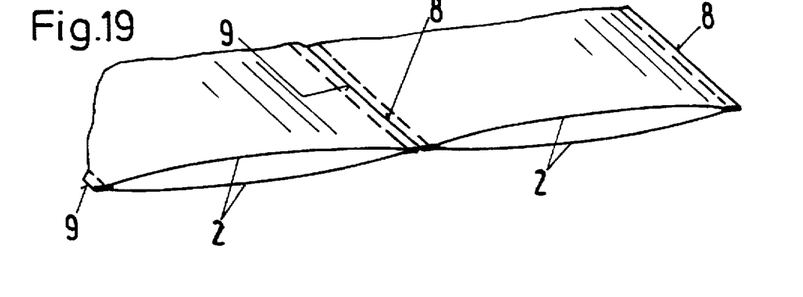
FIG. 19 is view showing a section taken along the lines XIX—XIX in FIG. 18.

A fiber material runs from a further supply roller 20 and is glued in individual blanks 7 on the upper surface 6 of the foil hose 2. This foil hose 2 is formed in accordance with FIGS. 18 and 19 from a lower foil web 21 as considered in the drawing plane of FIG. 11 and a second foil web 22 folded over it, as can be seen in FIGS. 13 and 18. For forming the offset regions 13, 14 shown in FIGS. 5–10, the foil hose 2 is provided with a separating welding at the latter side edges 8, 9 of the operation table cover 1 under the reversed rim 5 and in the vicinity of the bottom region 3, whereby the relatively small longitudinal over refuse regions 24, 25 are separated by a separating welding. Due to the separating welding, the both foil webs 21, 22 of FIG. 11 are closely connected with one another at the edges 24a, 25a of the separated regions 24, 25.

In the subsequent manufacturing step which however can be performed simultaneously with the preceding steps, a perforation welding seam 26 extending transversely to the transporting direction in accordance with the arrow 23 between both refuse regions 24, 25 is provided. Simultaneously, at its both sides, the foil webs 21, 22 are connected with one another by welding in the immediate vicinity of the perforation welding seam 26 and thereby closed at these locations.

As can be seen from the right half of the drawing of FIG. 11, the foil hose 2 is subjected to a first longitudinal folding. Therefore, the bottom region 3 comes to abutment under the later reversed rim 5 and the blank of the fiber material 7 is arranged in a protected position. After the production of the longitudinal fold 27, the individual blanks of the latter operation table cover 1 are connected both at their perforation welding seams 26 as well as continuously in the head region 4 as shown in FIG. 14.

Figure 16:
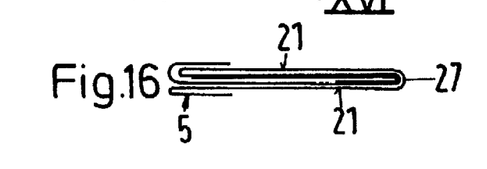
FIG. 16 is a view showing a section taken along the lines XVI—XVI in FIG. 12.

As can be seen from FIG. 12 in connection with FIGS. 15 and 16, the foil web 22 is then folded in direction of the arrow 28 and after this the foil web 21 is folded in direction of the arrow 29 for forming the reversed rim 5. After this, each reversed rim 5 is provided at its both side edges 5a, 5b (see FIGS. 5 and 7) with perforation welding seams 30, and simultaneously closed at both sides by the throughgoing welding seams. Up to this manufacturing phase, in accordance with the arrow 31 in FIG. 2 the individual portions of the operation table cover 1 are closed at their perforation welding seams 26 in the central region 15 as well as by the further perforation welding seams 30 at their reversed rims 5. Thereby during drawing of the foil hose 2 in the transporting direction of the arrow 23, no drawing stresses which can lead to rejected products can occur. The reason is that the foil hose 2 can be further transported by not shown drawing rollers or bands over the whole length of the side edges 8, 9 with its superimposed foil webs 21, 22 uniformly and with continuous pulling forces. Then, the individual blanks of the operation table cover are simultaneously separated into individual products 32, for example by acceleration rollers, both in their central region 15 as well as at the reversed rim 5 at their perforation welding seams 26, 30. After a two-time longitudinal folding in accordance with the folds 33, 34 of FIG. 17 they are subjected to at least one two-time transverse folding until they can be reduced to the form 35 of a ready to use folding pack 35.

FIG. 17 also shows a metal plate 37 which is inserted for protection of the lower regions of the operation table cover 1, when it is necessary to produce the perforation welding seam 30 on the reversed rim 5 at the height of the arrow 31.

In accordance with another alternative of the inventive method, in the manufacturing phase 31 the assembled blanks of the individual operation table covers 1 remain connected at their perforation welding seams 26, 30 and wound on a not shown roller. From this roller they can be then removed as tearing-off products for the known set packs.

FIG. 18 shows an enlarged fragment 18 of FIG. 11 with two foil webs 21 and 22 assembled in the head region 4. They are connected at the side edges 8, 9 in the central region 15 by a perforation welding seam 26. This operation table covers 1 are closed in their bottom region 3 by the folding edge 13 shown in FIG. 5.

Figure 20:
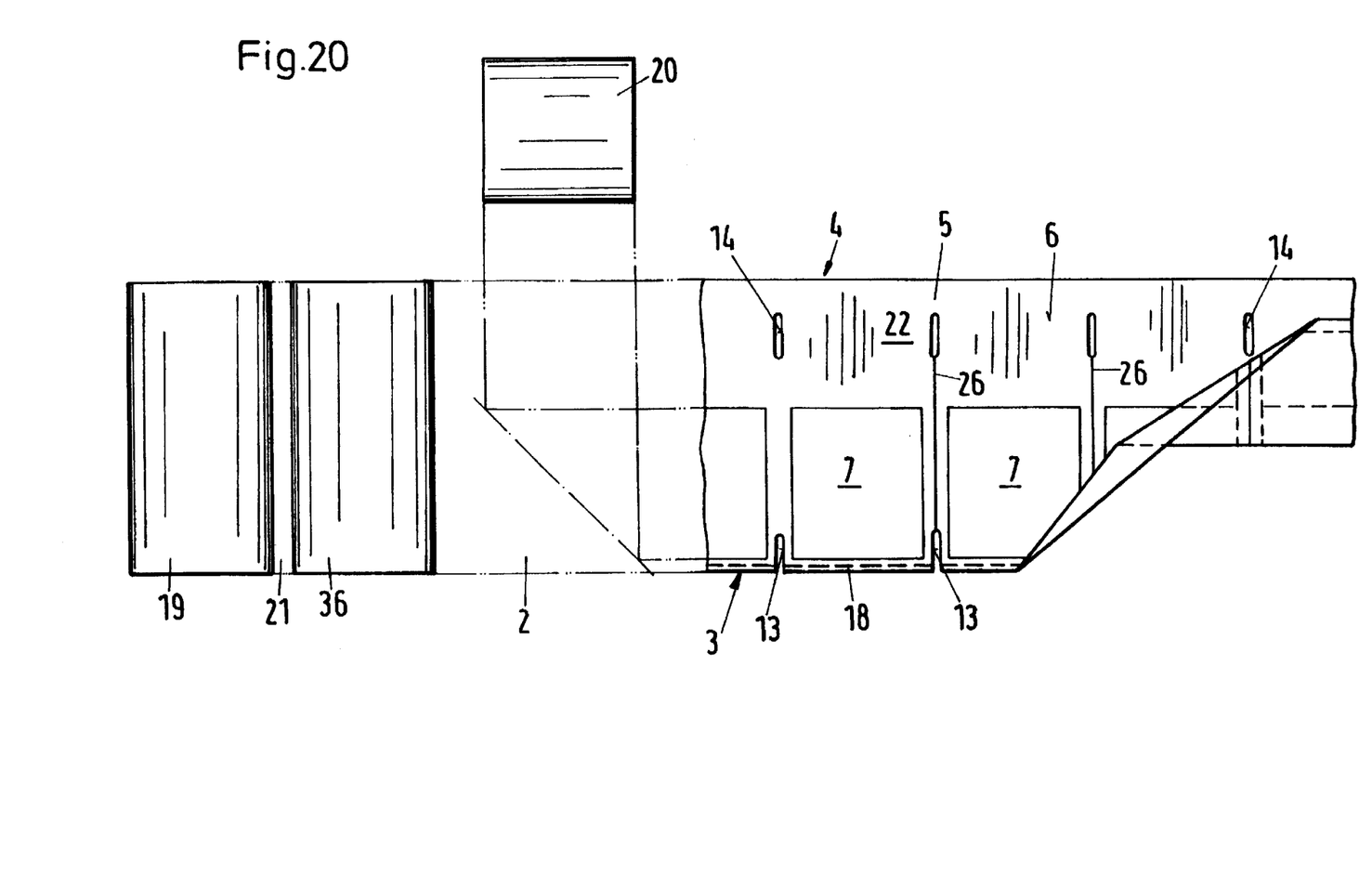
FIG. 20 is a view of a foil hose substantially corresponding to the view of FIG. 18 and formed from two congruent individual foils arranged over one another.

As can be seen from FIG. 20 the foil hose 2 is formed of two congruent superimposed individual foils 21, 22 which are drawn from two supply rollers 19, 36. They are connected with one another in the bottom region 3 with a throughgoing welding seam 18 as can be seen from FIGS. 7–10. The operation table covers shown there are formed from foil hoses 2 in accordance with the method of FIG. 20.

It will be understood that each of the elements described above, or two or more together, may also find a useful application in other types of constructions and methods differing from the types described above.

While the invention has been illustrated and described as embodied in a operation table cover and method of producing the same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An operation table cover, comprising a foil hose of a thermoplastic material having a closed bottom region, an open head region provided with a circumferential reversed rim, and side edges connected with one another by welding seams, said side edges in the vicinity of said bottom region and directly under said reversed rim being provided with inwardly directed offset regions which form a central region therebetween, said reversed rim having a width corresponding to a width of said central region located between said offset regions.

2. An operation table cover as defined in claim 1, wherein said offset regions in said side edges have length under said reversed rim which is insignificantly greater than a length of said reversed rim.

3. An operation table cover as defined in claim 1, wherein said regions in said side edges have a length in the vicinity of said bottom region which is equal to a length of said reversed rim.

4. An operation table cover as defined in claim 1, wherein said regions in said side edges have a length in the vicinity of said bottom region which is insignificantly smaller than a length of said reversed rim.

5. An operation table cover as defined in claim 1, wherein said regions in said side edges have a length in the vicinity of said bottom region which is insignificantly greater than a length of said reversed rim.

6. An operation table cover as defined in claim 1, wherein said offset regions have ends which merge into said side edges of said central region and said reversed rim in form of a rounding.

7. An operation table cover as defined in claim 6, wherein said rounding is formed as a quarter circle.

8. An operation table cover as defined in claim 1, wherein one of said offset regions has a width under said reversed rim which is equal to a width of the other of said offset regions in the vicinity of said bottom region.

9. An operation table cover as defined in claim 1, wherein said bottom region has a folding edge.

10. An operation table cover as defined in claim 1, wherein said bottom region has a welding seam which closes said bottom region.

11. A method for producing an operation table cover of a foil hose composed of thermoplastic material with a closed longitudinal edge in a bottom region and an open longitudinal edge in a head region, comprising the steps of drawing a foil hose in a transporting longitudinal direction by drawing means; providing welding seams and recesses extending transversely to the transporting direction; forming a reversed rim in the head region after a longitudinal folding in a central region and two longitudinal folds at opposite sides; connecting side edges of said reversed rim by welding seams; subjecting the foil hose to a separating welding for forming offset regions at side edges of the operation table cover under the reversed rim and in the vicinity of the bottom region; providing the foil hose in the central region of the side edges between the offset regions with a perforation welding seam extending transversely to the longitudinal transporting direction and closing both sides by welding; providing the reversed rim before separation of individual operation table covers at its both side edges with perforation welding seams and closing both sides by welding.

12. A method as defined in claim 11; and further comprising the step of simultaneously separating the perforation welding seams in the central region and at the reversed rim.

13. A method as defined in claim 11; and further comprising the step of reducing the operation table covers their separation by further longitudinal and transverse folding to a ready to use folding pack.

14. A method as defined in claim 11; and further comprising the step of rolling the connected operation table covers after producing of the perforation welding seams in the central region and at the reversed rim on a roller; and then tearing off of the operation table covers along their perforation welding seams in the central region and at the reversed rim.

15. A method as defined in claim 11, wherein the reversed rim is provided with a perforation welding seam and closed at both sides by welding after a further longitudinal folding with interposition of a supporting metal plate between the central region and the reversed rim longitudinally folded on it.

16. A method as defined in claim 11, wherein the foil hose is composed of a single layer synthetic plastic foil which is folded exactly in its center parallel to the transporting direction.

17. A method as defined in claim 11, wherein the foil hose is composed of two congruent superimposed individual foils which are provided in the bottom region with a continuous welding seam extending parallel to the transporting longitudinal direction.

* * * * *